(12) United States Patent
Kang et al.

(10) Patent No.: US 10,793,888 B2
(45) Date of Patent: Oct. 6, 2020

(54) IN VITRO METHOD FOR FAST SCARLESS DNA ASSEMBLY USING THERMOSTABLE EXONUCLEASES AND LIGASE

(71) Applicants: Zhen Kang, Wuxi (CN); Jian Chen, Wuxi (CN); Peng Jin, Wuxi (CN); Guocheng Du, Wuxi (CN); Wenwen Ding, Wuxi (CN)

(72) Inventors: Zhen Kang, Wuxi (CN); Jian Chen, Wuxi (CN); Peng Jin, Wuxi (CN); Guocheng Du, Wuxi (CN); Wenwen Ding, Wuxi (CN)

(73) Assignee: Jiangnan University, Wuxi, JS (CN)

( * ) Notice: Subject to any disclaimer, the term of this patent is extended or adjusted under 35 U.S.C. 154(b) by 388 days.

(21) Appl. No.: 15/347,750

(22) Filed: Nov. 9, 2016

(65) Prior Publication Data
US 2017/0175156 A1 Jun. 22, 2017

(30) Foreign Application Priority Data

Dec. 22, 2015 (CN) .......................... 2015 1 0969678
Jul. 11, 2016 (CN) .......................... 2016 1 0543258

(51) Int. Cl.
  *C12P 19/34* (2006.01)
  *C12Q 1/6806* (2018.01)
  *C12N 15/10* (2006.01)

(52) U.S. Cl.
  CPC .......... *C12P 19/34* (2013.01); *C12N 15/1031* (2013.01); *C12Q 1/6806* (2013.01)

(58) Field of Classification Search
  None
  See application file for complete search history.

(56) References Cited

U.S. PATENT DOCUMENTS

2011/0111413 A1* 5/2011 Padgett ................ C12N 15/102
                                                                     435/6.12
2013/0225451 A1* 8/2013 Gibson .............. C12N 15/1093
                                                                     506/26

OTHER PUBLICATIONS

Jin et al. DATEL: A scarless and sequence-independent DNA assembly method using thermostable exonucleases and ligase. ACS Synth. Biol., vol. 5, p. 1028-1031, 2016 and supplementary data.*
Stemmer et al. Single-step assembly of a gene and entire plasmid from large numbers of oligodeoxyribonucleotides. Gene, vol. 164, p. 49-53, 1995.*
Shaw-Smith et al. Improved method for detecting differentially expressed genes using cDNA indexing. Biotechniques, vol. 28(5), p. 958-964, 2000.*

* cited by examiner

*Primary Examiner* — Kenneth R Horlick
(74) *Attorney, Agent, or Firm* — Lili Chen

(57) ABSTRACT

The present invention provides a method for scarless in vitro DNA assembly using thermostable exonucleases and ligase, which relates to the field of genetic engineering. The present invention provides a fast method for assembling DNA subfragments with homologous ends, which employs thermostable polymerases and ligase in a thermal cycle of denaturation, annealing, digestion and ligation. After denaturation, DNA subfragments are assembled together via annealing of the homologous end sequences, the unpaired single-stranded overhangs are digested by polymerases, and the resulting nicked gaps are sealed by a ligase. Using this method, 2-6 DNA subfragments were successfully assembled within two hours. This method can be used in conventional DNA recombination and be adapted to high throughput assembly operations. In addition, combinatorial mutations can be easily introduced into the assembled sequence by use of primers with mutated bases. It is particularly suitable for making enzyme and synthetic pathways mutation libraries with high diversity, which can be used in directed evolution to screen for enzymes and synthetic pathways with desirable properties.

11 Claims, 10 Drawing Sheets

Specification includes a Sequence Listing.

IN VITRO METHOD FOR FAST SCARLESS DNA ASSEMBLY USING THERMOSTABLE EXONUCLEASES AND LIGASE

CROSS-REFERENCES AND RELATED APPLICATIONS

This application claims the benefit of priority to Chinese Application No. 201510969678.5, entitled "An in vitro method for fast scarless DNA assembly using thermostable exonucleases and ligase", filed Dec. 22, 2015, and the benefit of priority to Chinese Application No. 201610543258.5, entitled "A novel method for fast non-phosphorylated DNA assembly", filed Jul. 11, 2016, the contents of which are herein incorporated by reference in their entirety.

BACKGROUND OF THE INVENTION

Field of the Invention

The present invention relates to the field of genetic engineering, which particularly relates to a method for fast and scarless DNA assembly using thermostable exonucleases and ligase.

Description of the Related Art

The discovery of restriction endonuclease and DNA ligase is one of the significant achievements in the field of molecular biology in last century, which provides a technical foundation for recombinant DNA technologies. The recombinant DNA techniques have greatly accelerated the understanding of gene structure and functions, which laid the foundation for the rapid development of enzyme engineering, metabolic engineering, and synthetic biology. However, due to the limitation of restriction enzyme sites and tedious steps of cloning operations, assembly of multiple DNA fragments is difficult to achieve with traditional recombinant DNA techniques, which is far from meeting the demand for rapid assembly of multiple DNA elements in construction of complex metabolic pathways and regulatory components in modern metabolic engineering and synthetic biology. Therefore, there is an urgent need for developing techniques for rapid assembly of multiple sequence-independent DNA fragments.

With the development of molecular biology and gene engineering technology, exonucleases that cleave DNA sequence from one end of the sequence and result in sticky ends have been discovered, which leads to development of sequence- and ligation-independent cloning (SLIC) techniques. The SLIC techniques has been widely applied in the field of biosynthesis and metabolic engineering. The classic SLIC method using T4 DNA polymerase or T5 exonuclease, has been widely used in the large-scale gene cloning and vector construction. Typically, specific regions (≥15 nt) homologous to the end sequence of neighboring DNA fragment was added to the ends of DNA fragments, which are used as the recombination site. These homologous sequences are based on the end sequence of the neighboring DNA fragments, and are not limited by any internal sequences of the DNA fragments. The DNA fragments were digested with T4 DNA polymerase and T5 exonuclease to generate 5' or 3' overhangs. The homologous 5' or 3' overhangs bind to each other stably during the annealing process. The annealed fragments form a complete circular plasmid with the aid of the DNA repair system in *Escherichia coli*. The one-step isothermal assembly technology was later developed to use DNA polymerase to fill the gaps and DNA ligase to seal the nicks. In this method, T5 exonuclease cuts from the 5' end of double-stranded DNA fragments, resulting in a 3' sticky end. The complementary sticky ends of two DNA fragments bind to each other, the gaps are filled by DNA polymerases and the nicks are ligated by DNA ligases, achieving a seamless double-stranded DNA. This sequence-independent assembly technique has significantly improved the assembly efficiency. However, the length of single-stranded DNA obtained from above techniques couldn't been accurately controlled, which makes it not appropriate for assembly of short fragments. Besides, with three enzymes involved in the assembly process, the assembly efficiency of more than 4 fragments declines rapidly.

Assembly methods using different types of restriction enzymes have also been developed, such as Golden Gate assembly and assembly methods based on nicking enzymes. Although one-step assembly for 6-10 fragments could be realized through these methods, they were limited by the availability of restriction enzyme sites. In addition, the overlapping regions of those fragments contain a 6-10 bp scar sequence of the restriction enzyme sites. Also, an assembly method based on yeast homologous recombination has been developed. In this method, overlapping end sequences of specific length (≥40 nt) are added to neighboring DNA fragments or the vector during PCR amplification. All of the DNA fragments with overlapping ends and the vector of yeast were electrotransformed into *Saccharomyces cerevisiae*. Up to 25 DNA fragments can be assembled in a scarless and sequence-independent mode. This technique is extremely attractive for application in synthetic biology and metabolic engineering. However, the requirement of the long homologous region increases the cost for primer synthesis, and it is time-consuming to perform the DNA assembly method in strains other than *S. cerevisiae*.

A sequence-independent and scarless assembly method with high efficiency and accuracy, which can be adapted to high-throughput automation, is needed for synthetic biology applications.

DETAILED DESCRIPTION

The present invention provides a method for fast scarless DNA assembly of 2-10 fragments using thermostable exonucleases and ligase, which can be applied in generating combinatorial gene mutations.

The present invention comprises the following steps: generating to-be-assembled dsDNA subfragments with overlapping ends through PCR amplification; and connecting the dsDNA subfragments through a thermal cycle of denaturation, annealing, digestion, and ligation. The overlapping ends refer to 3' and 5' end sequences of a DNA subfragment that are homologous to 5' end sequence of its downstream DNA subfragment and 3' end sequence of its upstream DNA subfragment, respectively. The length of the overlapping sequences varies from 20 to 70 bp. The DNA subfragments can be structural genes or vectors. The overlapping end sequences come from the naturally existing sequences of the target DNAs. No foreign sequences or restriction enzyme recognition sites are added into the assembled sequence, thus resulting in a scarless assembly.

Using primers with specific end sequences, DNA subfragments with overlapping ends (20-70 bp) are amplified through PCR reactions. The overlapping end sequences enable these subfragments to anneal in a defined order during DNA assembly (see FIG. 1). The DNA assembly is achieved through a thermal cycle, which includes denaturing dsDNA subfragments, annealing DNA subfragments via overlapping ends, digesting single-stranded overhang sequences, and ligating nicked gaps to generate an assembled sequence.

The thermal cycle reaction is carried out in a buffer solution suitable for all the enzymes involved. The thermal cycle reaction has 1-15 cycles, wherein each cycle comprises denaturing at 98-85° C., annealing at 35-70° C., digesting at 45-72° C. for 5-35 min, and ligating at 40-68° C. for 1-10 min. The digestion of single-stranded DNA overhang is carried out using thermostable DNA exonucleases with 5'-3' or 3'-5' exonuclease activity. The ligation is carried out using a thermostable DNA ligase with ability to covalently seal the nicked gaps.

In one embodiment, primers are designed to generate DNA fragments with 30 bp overlapping end sequences.

In one embodiment, primers for amplifying DNA subfragments contain one or more mutations, which can be used to introduce mutations into the assembled sequence at the sites connecting two DNA subfragments. The mutated nucleotides may locate outside the overlapping region (see FIG. 5).

In one embodiment, the hydroxyl groups at the 5' end of primers or subfragments are phosphorylated by T4 polynucleotide kinase.

In one embodiment, the thermostable DNA exonuclease is Taq DNA polymerase with 5'->3' exonuclease activity or Pfu DNA polymerase with 3'->5' exonuclease activity.

In one embodiment, the thermostable DNA ligase is Taq DNA ligase,

In one embodiment, the thermal cycle is carried out in Taq DNA ligase solution containing 20 mM Tris-HCl, 25 mM potassium acetate, 10 mM magnesium acetate, 10 mM DTT, 1 mM NAD and 0.1% Triton X-100 (pH 7.6).

In one embodiment, the thermal cycle is carried out in modified Taq DNA ligase buffer (MTL buffer), containing 20.0 mM Tris-HCl, 25.0 mM KCl, 5.0 mM $MgCl_2$, 1.5 mM $NAD^+$, 0.1% Triton X-100.

In one embodiment, the DNA fragments and primers for PCR are not phosphorylated.

In one embodiment, the denaturation temperature in the thermal cycle is 94° C., the annealing temperature is 50° C., the digestion is carried out at 68° C. for 30 min, the ligation carried out at 50° C. for 5 min, and the reaction cycle is 3.

In one embodiment, the DNA assembly is carried out in a 15 μL reaction system containing 50 ng dsDNA subfragments, 1.5 μL 10×Taq DNA ligase buffer (200 mM Tris-HCl, 250 mM potassium acetate, 100 mM magnesium acetate, 100 mM DTT, 10 mM NAD and 1% Triton X-100, pH 7.6), 0.2 μL Pfu DNA polymerase, 0.2 μL Taq DNA polymerase, and 1 μL Taq DNA ligase. The reaction system is mixed and performed with the following conditions: 2 min at 94° C.; 3 cycles of 30 s at 94° C., 1 min at 50° C., 30 min at 68° C., and 5 min at 50° C.; and 10 min at 66° C.

The present invention could be used for DNA assembly, construction of biosynthesis pathways, protein assembly and combinatorial construction of pathways. The resulting product can be stored at −20° C. or introduced into competent cells.

The present invention provides a method for in vitro assembly of DNA fragments using a thermostable ligase and DNA polymerases. DNA Subfragments that contain overlapping end sequences with those of neighboring subfragments are generated by PCR amplification. The subfragments are subjected to a thermal cycle that includes denaturation, annealing, digestion and ligation, which results in a seamless DNA assembly. As shown in FIG. 1, each subfragment possesses 20-30 bp homologous sequences at both ends that match to those of the neighboring subfragments. The homologous sequences of neighboring subfragments anneal to each other at the annealing temperature after denaturation, resulting in a single-stranded "flap" structure with 3' or 5' overhangs. The 3' and 5' overhangs can be cleaved by Taq DNA polymerase and Pfu DNA polymerase, generating an assembled sequence with nicked gaps. The thermostable Taq DNA ligase seals the nicked gaps to form a fully assembled sequence without any foreign "scar" sequence. Since the enzymes used are thermostable ones, the thermal cycle (denaturation-annealing-digestion-ligation) can be repeated multiple times to increase the amount of the assembled sequences.

The present invention can also be applied in construction of DNA mutation libraries, such as protein mutation libraries or mutation libraries for metabolic pathways. It employs PCR primers to introduce degenerated or mutated bases into the end sequences of subfragments, thus building libraries of mutated subfragments. The mutated subfragments are then assembled into a complete sequence using the one-step assembling thermal cycle. The present method can be applied to build combinatorial mutation libraries for proteins or synthetic pathways with great diversity.

Compared to other assembly technologies, the present invention of fast scarless DNA assembly overcomes the limitation of sequence-dependence, time-consuming, low efficiency, and high costs. Using the method of the present invention, two to six fragments can be efficiently assembled in 2 hours. The present invention can be applied to conventional DNA recombination and adapted to high-throughput assembly operation. It is especially suitable for introducing diverse mutations into enzymes or synthetic pathways that can be used in directed evolution of proteins and metabolic pathways.

EXAMPLES

Figure 1:
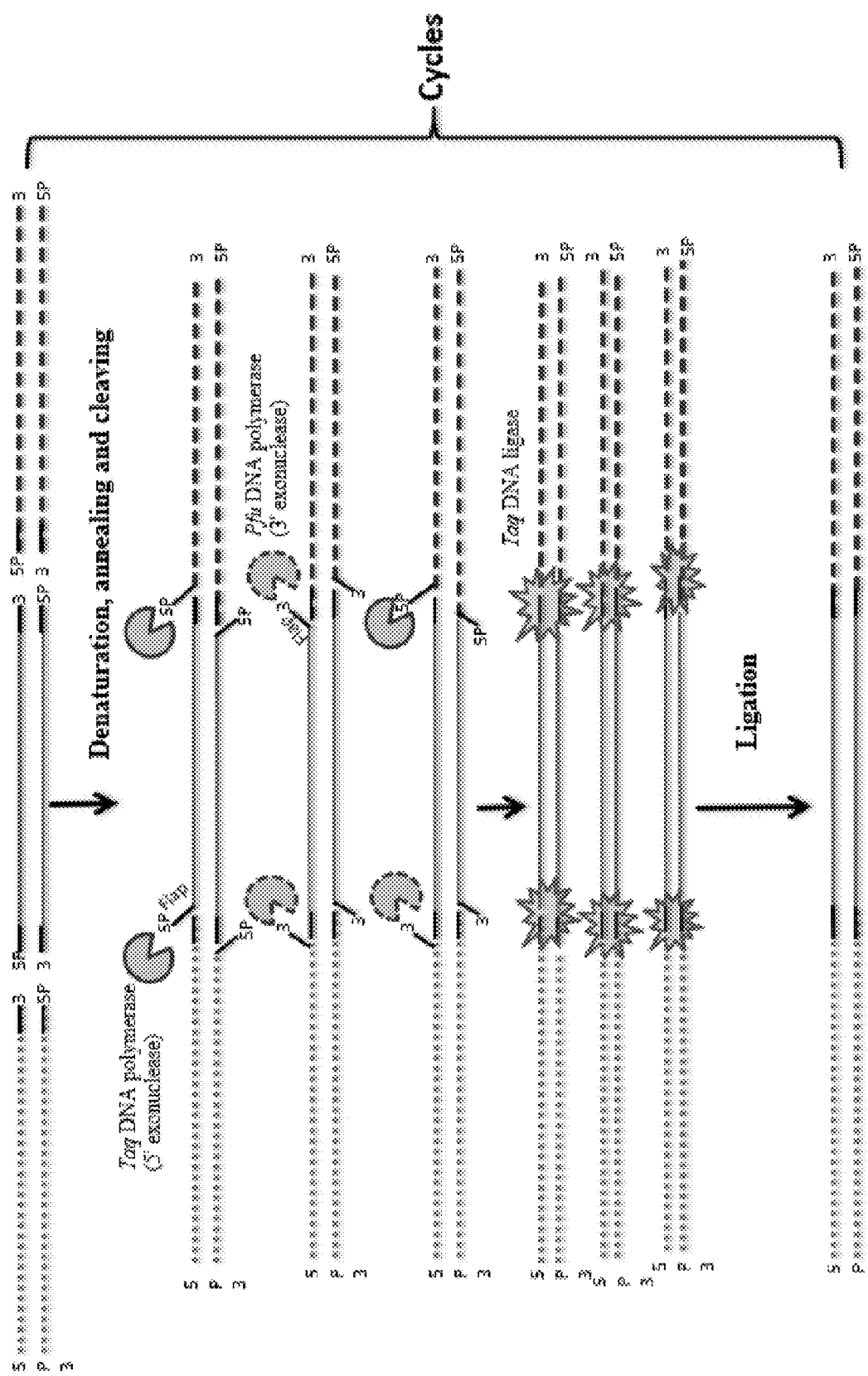
FIG. 1. Illustrative diagram of the DATEL assembly technique of the present invention.

Example 1. Optimization of DATEL Assembly Reaction System

Gene gfp encoding a green fluorescent protein and plasmid pUC19 were used for optimization of DATEL reaction system, in terms of the overlaps' length and the digesting time. Six pairs of primers (Seq ID NOs: 3-14) were designed for amplifying gfp, each carrying a 20 bp, 30 bp, 40 bp, 50 bp, 60 bp or 70 bp overlapping sequence with plasmid pUC19. One pair of primer (Seq ID NO: 1 & 2) were designed for amplifying plasmid pUC19. The primers were shown as follows:

```
TEL/puc19-F (Seq ID NO: 1):
TTCTTCTCCCTTACCCATGGCGTAATCATGGTCATAGCTGTTTCCT

TEL/puc19-R (Seq ID NO: 2):
TGGATGAACTATACAAATAACTGGCCGTCGTTTTACAACGTCG

TEL/gfp-P20F (Seq ID NO: 3):
CCATGGGTAAGGGAGAAGAACTTTTCAC

TEL/gfp-P20R (Seq ID NO: 4):
TTATTTGTATAGTTCATCCATGCC

TEL/gfp-P30F (Seq ID NO: 5):
CATGATTACGCCATGGGTAAGGGAGAAGAA

TEL/gfp-P30R (Seq ID NO: 6):
CGACGGCCAGTTATTTGTATAGTTCATCCA

TEL/gfp-P40F (Seq ID NO: 7):
CAGCTATGACCATGATTACGCCATGGGTAAGGGAGAAGAA

TEL/gfp-P40R (Seq ID NO: 8):
CGTTGTAAAACGACGGCCAGTTATTTGTATAGTTCATCCA

TEL/gfp-P50F (Seq ID NO: 9):
ACACAGGAAACAGCTATGACCATGATTACGCCATGGGTAAGGGAGAAGAA

TEL/gfp-P50R (Seq ID NO: 10):
CCAGTCACGACGTTGTAAAACGACGGCCAGTTATTTGTATAGTTCATCCA TEL/gfp-P60F (Seq ID NO: 11):
TAACAATTTCACACAGGAAACAGCTATGACCATGATTACGCCATGGGTAA
GGGAGAAGAA TEL/gfp-P60R (Seq ID NO: 12):
CAGGGTTTTCCCAGTCACGACGTTGTAAAACGACGGCCAGTTATTTGTAT
AGTTCATCCA TEL/gfp-P70F (Seq ID NO: 13):
TGTGAGCGGATAACAATTTCACACAGGAAACAGCTATGACCATGATTACG
CCATGGGTAAGGGAGAAGAA TEL/gfp-P70R (Seq ID NO: 14):
TGGGTAACGCCAGGGTTTTCCCAGTCACGACGTTGTAAAACGACGGCCAG
TTATTTGTATAGTTCATCCA
```

The primers and DNA fragments were phosphorylated in 50 µL reactions containing 100 pmol of primers (or 1 µg DNA fragments), 1×T4 DNA ligase buffer (NEB, New England Biolabs, Ipswich, Mass., USA), and 8 U of polynucleotide kinase (NEB). The reaction was incubated at 37° C. for 30 min, and terminated by heating at 75° C. for 10 min.

Each primer was phosphorylated through above steps. Primer TEL/puc19-F and TEL/puc19-R were used for amplifying vector fragment pUC19. The above six pairs of gfp primers were used for amplifying six gfp fragments. The to-be-assembled vector fragments were amplified from the same vector using corresponding PCR primes as described above. The to-be-assembled gene fragments (e.g. gfp gene in this Example) were amplified from constructs containing the gene of interest using corresponding primers to add overlapping end sequences of a particular length. In this example, primer pairs of TEL/gfp-P20F and TEL/gfp-P20R, TEL/gfp-P30F and TEL/gfp-P30R, TEL/gfp-P40F and TEL/gfp-P40R, TEL/gfp-P50F and TEL/gfp-P50R, TEL/gfp-P60F and TEL/gfp-P60R, and TEL/gfp-P70F and TEL/gfp-P70R were used to amplify gfp genes with overlapping sequences of 20 bp, 30 bp, 40 bp, 50 bp, 60 bp and 70 bp, respectively. Each gfp PCR fragment possessed homologous end sequences that overlap to the end sequences of pUC19 vectors with an overlapping length varying from 20 to 70 bp. The PCR reaction was performed in a 50 µL volume containing 1 µL (10 µmol) of each primer, 25 µL of 2×super Pfu DNA polymerase mix (Hangzhou Biosci Co., Zhejiang, China), and double-distilled water. The reaction was performed with the following PCR conditions: 4 min at 94° C. for pre-denaturation; 32 cycles of 30 sec denaturation at 94° C., 30 sec at 58° C., and 5 min at 72° C.; and final 5 min at 72° C. The resulting solution were then incubated at 37° C. for 30 min with 1 µL DpnI restriction enzyme to digest DNA fragments. Following electrophoresis, the PCR products were gel purified from 1% agarose gel using a Gel Purification Kit (Hangzhou Biosci Co). Concentration of nucleic acids were measured using NanoDrop 2000 spectrophotometer (Thermo Scientific, Wilmington, Del., USA).

The DATEL reaction was performed in a 15 µL volume containing 1.5 µL 10×Taq DNA ligase buffer (NEB), 50 ng gfp fragment, 50 ng pUC19, 0.2 µL Pfu super DNA polymerase, 0.2 µL Taq DNA polymerase, 1 µL Taq DNA ligase, and 1.5 µL of Taq DNA ligase buffer. The DATEL assembly was performed with the following thermal cycles: 2 min at 94° C.; 3 cycles of 30 s at 94° C., 1 min at 45° C., 5-35 min at 68° C., and 5 min at 50° C.; and final 10 min at 66° C. The assembled product could be stored at −20° C. or immediately transferred into competence cells plated on the LB medium containing 100 µg/mL ampicillin and cultured overnight at 37° C. The resulting colonies were then confirmed with PCR using gene-specific primers. In this example, the effects of the length of overlapping end sequences and the exonuclease digestion time on the assembly efficiency were analyzed. The digestion time tested were for 5 min, 10 min, 15 min, 20 min, 25 min, 30 min, and 35 min at 68° C.

Figure 2:
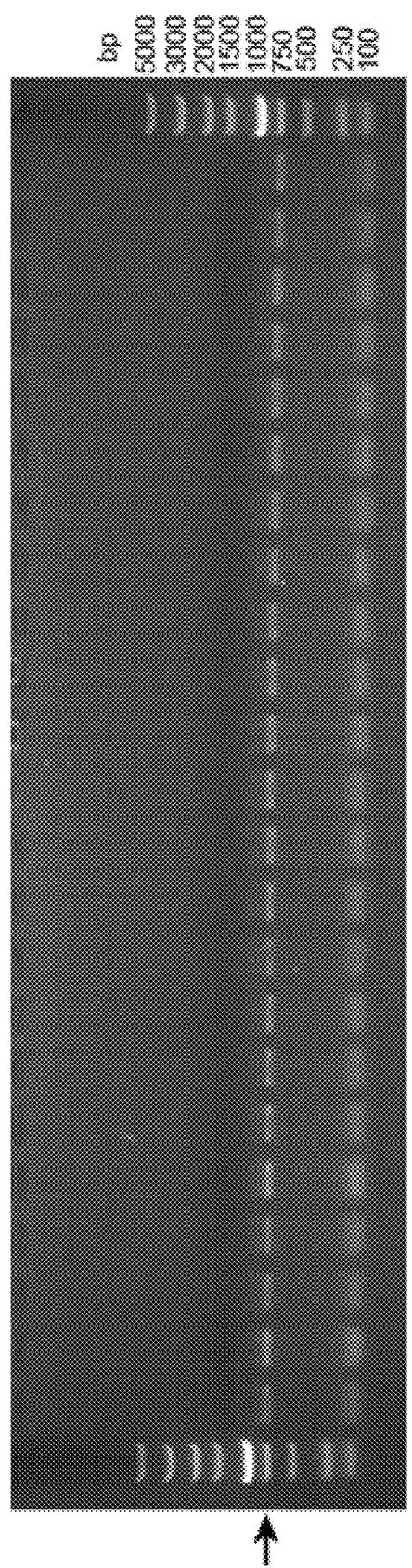
FIG. 2. Gel electrophoresis verification of assembly accuracy of fragments gfp and pUC19. The arrow indicates the position of the correct assembly.
Figure 3:
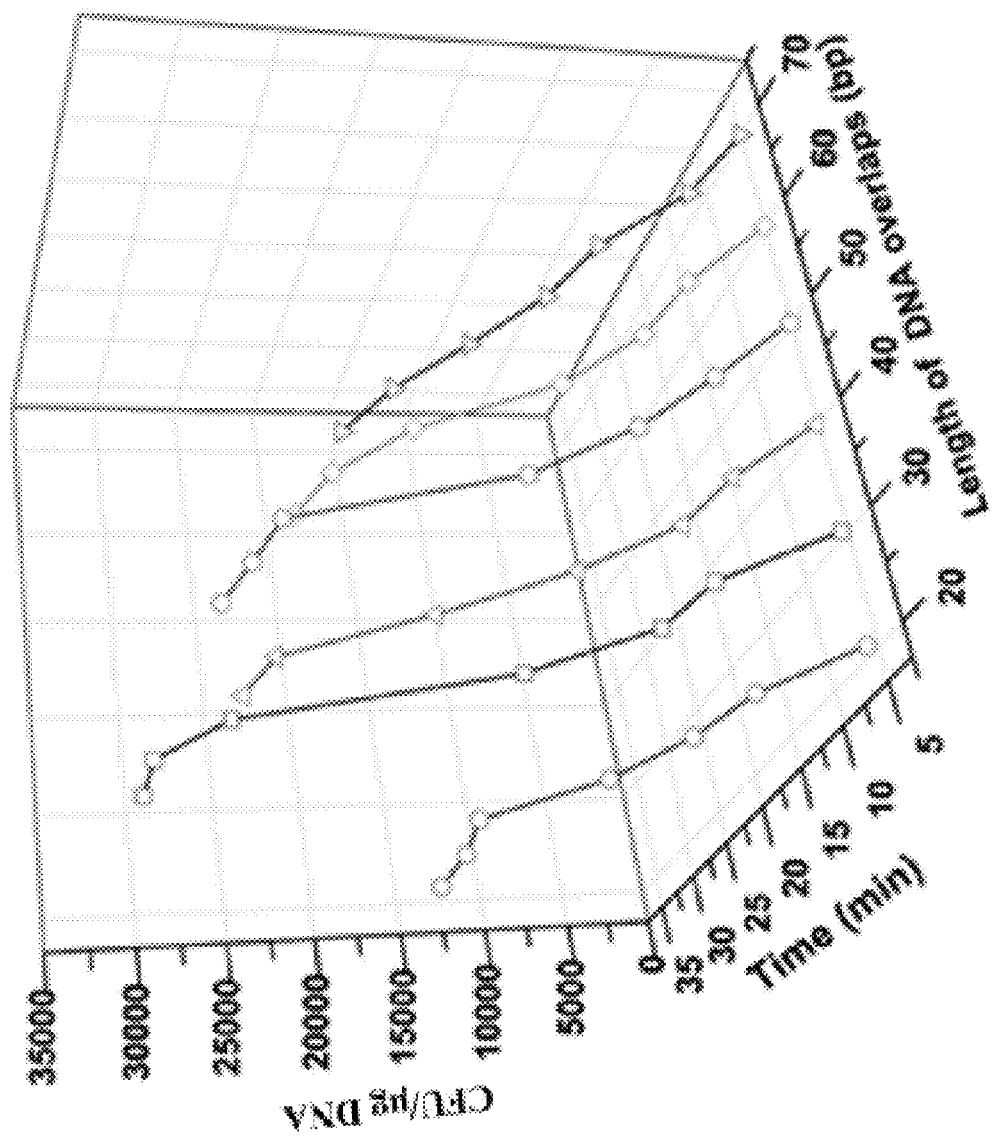
FIG. 3. Effects of the digestion time and the length of overlapping sequences to the assembly efficiency of the DATEL techniques.

As shown in FIG. 2, each of 132 randomly selected colonies were correctly assembled. Further sequencing analysis of the assembled colonies confirmed 100% accuracy of recombination of two DNA fragments using the DATEL technique. The CFUs of the colonies were counted and analyzed. As shown in FIG. 3, fragments with 30 bp overlapping region showed the highest assemble efficiency, which reach to 29150 CFU per microgram. With the increasing time of reaction, the assembly efficiency improved significantly. The assembly efficiency of fragments with 30 bp homologous overlaps increased 2.29 times when its digestion time increased from 5 min to 30 min. However, longer digestion couldn't increased the assembly efficiency any more, indicating the 30 bp "flap" structure could be completely cleaved within 30 min by DNA polymerase.

Example 2. Multiple Fragment Fast Assembly by DATEL

DATEL technique was used to assemble the promoter PrpoS of rpoS from *E. coli*, three different estC23 genes (encoding three esterases), gfp (encoding a green fluorescent protein), kan (encoding kanamycin), and the pbluesscript II SK(+), which was used for evaluating its efficiency and accuracy in multiple fragment assembly. All the primers were firstly phosphorylated as described in Example 1. The primers were designed as the following:

```
MFA/pSK-R (Seq ID NO: 15):
GGTAATGGCAGTCGTGACTGGGAAAACCCTGGCGTTAC

MFA/pSK-4F (Seq ID NO: 16):
CTCGATGAGTTCTTCTAACCTGTGTGAAATTGTTATCCGCTCAC

MFA/pSK-3F (Seq ID NO: 17):
GTTCATCCGCGCCAACGCCGAGTAACCTGTGTGAAATTGTTATCCGCTCAC

MFA/pSK-2F (Seq ID NO: 18):
ATTACACATGGCATGGACGAACTATACAAATAACCTGTGTGAAATTGTTATCCGCTCAC

MFA/Prpos-F (Seq ID NO: 19):
AGGGTTTTCCCAGTCACGACTGCCATTACCCAGGCCGACGCAGC

MFA/Prpos-R (Seq ID NO: 20):
CTTCTCCCTTACCCATAAGGTGGCTCCTACCCGTGATC

MFA/gfp-F (Seq ID NO: 21):
GTAGGAGCCACCTTATGGGTAAGGGAGAAGAACTTTTCAC

MFA/gfp-R (Seq ID NO: 22):
TTATTTGTATAGTTCGTCCATGCCATG

MFA/est-F (Seq ID NO: 23):
ATTACACATGGCATGGACGAACTATACAAATAAATGTCACAACAACAGCTGAATCA MFA/est-R (Seq ID NO: 24):
TTACTCGGCGTTGGCGCGGATGAAC MFA/kan-F (Seq ID NO: 25):
GTTCATCCGCGCCAACGCCGAGTAAATGAGCCATATTCAACGGGAAACGTC MFA/kan-R (Seq ID NO: 26):
CAATTTCACACAGGTTAGAAGAACTCATCGAGCATC
```

The pBluescript II SK(+) vector for assembling 3, 4, or 5 DNA fragments were amplified by PCR reactions using phosphorylated primer pairs of MFA/pSK-R and MFA/pSK-2F, MFA/pSK-R and MFA/pSK-3F, and MFA/pSK-R and MFA/pSK-4F, respectively. The promoter PrpoS, gene estC23, gfp, and kan were also amplified by the corresponding primers (Seq ID NOs: 19-26). After the PCR reaction, the resulting solution were added with 1 μL DpnI restriction enzymes, mixed and incubated at 37° C. for 30 min to digest DNA fragments. The PCR product was purified from 1% agarose gel using a Gel Purification Kit. Nucleic acid concentration of the resulting vector and PCR fragments were measured by NanoDrop 2000.

Figure 4:
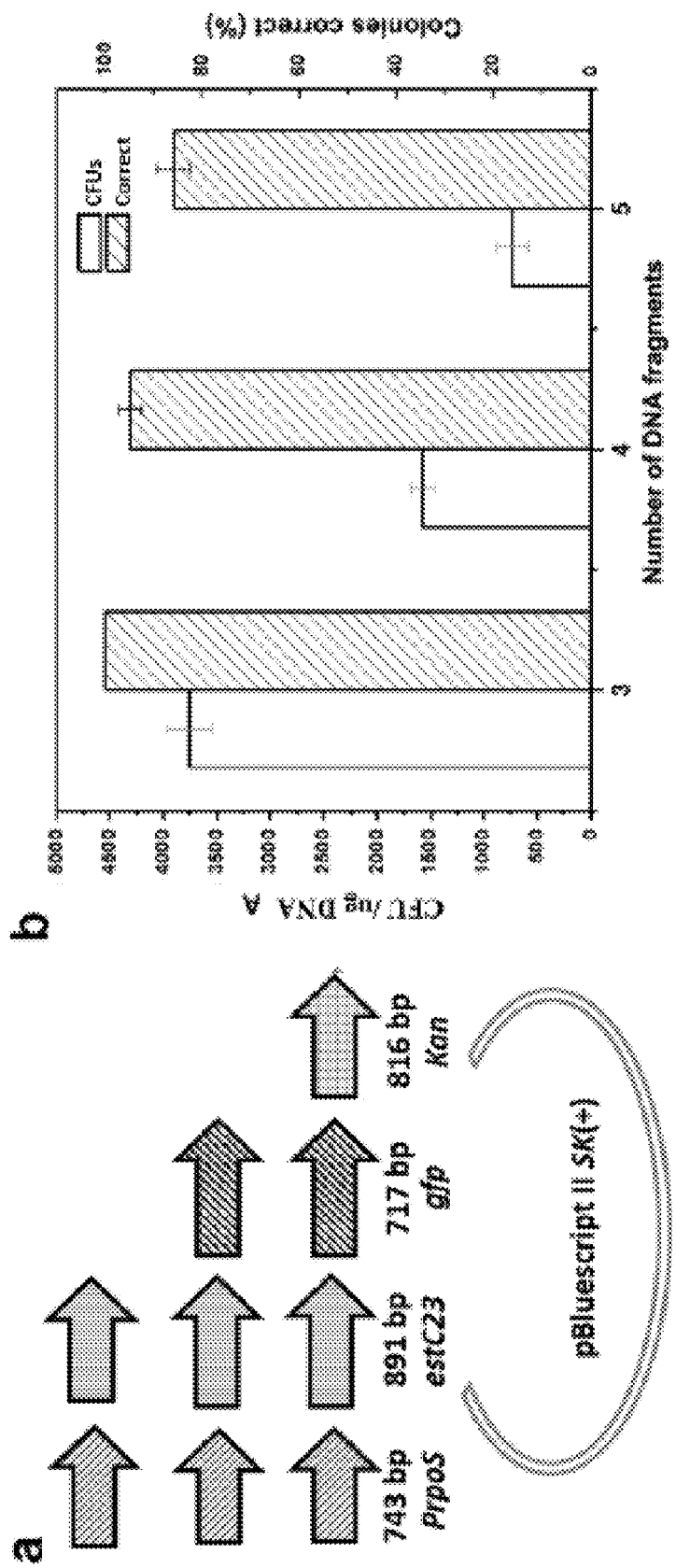
FIG. 4. (a) Diagram of multi-fragments assembly using the DATEL techniques; (b) Efficiency of multi-fragments assembly using the DATEL techniques.

The DATEL reaction was performed in a 15 μL volume containing 1.5 μL 10×Taq DNA ligase buffer (NEB), 0.2 μL Pfu super DNA polymerase, 0.2 μL Taq DNA polymerase, 1 μL Taq DNA ligase, and 50 ng of each DNA fragment and pSK vector (PrpoS, estC23, and vector pSK for 3 fragments assembly; PrpoS, estC23, gfp and vector pSK for 4 fragments assembly; and PrpoS, estC23, gfp, kan and vector pSK for 5 fragments assembly). The reaction was performed with the following thermal cycles: 2 min at 94° C.; 3 cycles of 30 s at 94° C., 1 min at 50° C., 30 min at 68° C., and 5 min at 50° C.; and final 10 min at 60° C. The resulting solution were transferred into competent cells, plated in LB medium containing 100 μg/mL ampicillin (recombinants with 5 fragment assembly were plated in a LB medium containing 100 μg/mL ampicillin and 50 μg/mL kanamycin) and incubated at 37° C. for 30 min. The CFUs of colonies were counted. As shown in FIG. 4b, the assembly efficiency was 4100, 1600 and 550 CFU/mg DNA for 3, 4 and 5 fragment assembly, respectively. The recombinants were selected randomly for PCR verification and DNA sequencing analysis. As shown in FIG. 4b, accuracy of assembly was 100%, 92% and 85% for 3, 4 and 5 fragment assembly, respectively. This shows that the DATEL assembly method has high assembly accuracy.

Figure 5:
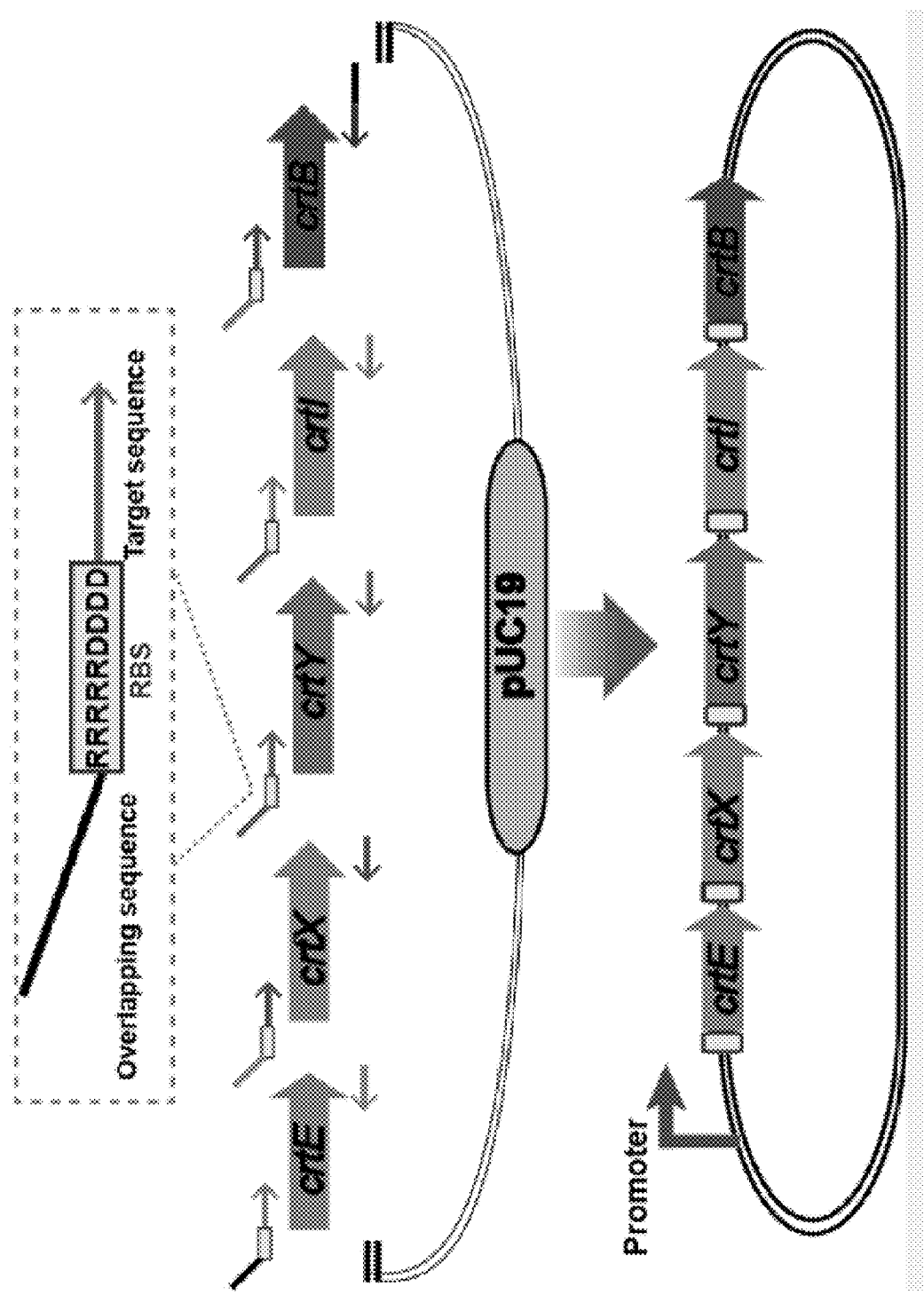
FIG. 5. Construction of β-carotene synthesis pathway combinatorial mutation libraries using DATEL assembly techniques.

Example 3. Construction of β-Carotene Synthesis Pathway Combinatorial Libraries Using DATEL The gene cluster crtEXYIB in β-carotene synthesis pathway from *Pantoea agglomerans* was used for assessing the capability of the DATEL assembly technique in multiple fragment assembly. The gene cluster include five DNA fragments, crtE, crtX, crtY, crtI and crtB (see FIG. 5). To use the DATEL technique to introduce combinatorial mutations into the synthesis pathway, the ribosome binding site (RBS) of the forward primer of each gene were designed to use degenerate nucleotides. The resulting PCR fragments thus contain an upstream RBS library with great variety in translation efficiency. The primers used in this example were as follows.

```
CPA/puc19-F (Seq ID NO: 27):
TGCCGGTATTTTCTCCTTACGCATCTGTGC

CPA/puc19-R (Seq ID NO: 28):
CCACACAACATACGAGCCGGAAGCATAAAG

CPA/crtE-F (Seq ID NO: 29):
CTTTATGCTTCCGGCTCGTATGTTGTGTGGRRRRRDDDDATGATGACGGTCTGTGCAGAACAACACG CPA/crtE-R (Seq ID NO: 30):
TTAACTGACGGCAGCGAGTTTTTCTC CPA/crtX-F (Seq ID NO: 31):
TTTGAGAAAAAACTCGCTGCCGTCAGTTAARRRRRDDDDATGAGCCACTTTGCGGTCATTGCACCGC CPA/crtX-R (Seq ID NO: 32):
TTAGACTGCTGCGTAGTCTCTCCTGGTGAGGACCGGCTG CPA/crtY-F (Seq ID NO: 33):
CTCACCAGGAGAGACTACGCAGCAGTCTAARRRRRDDDDATGCCGCGGTATGATCTGATTCTGG CPA/crtY-R (Seq ID NO: 34):
TCATTGCATCGCCTGTTGACGGTGAG CPA/crtI-F (Seq ID NO: 35):
CTCCTCACCGTCAACAGGCGATGCAATGADDRRRRRDDDDATGAATAGAACTACAGTAATTGGCG CPA/crtI-R (Seq ID NO: 36):
TCAAGCCAGATCCTCCAGCATCAATC
```

-continued

CPA/crtB-F (Seq ID NO: 37):
CAGGATTGATGCTGGAGGATCTGGCTTGADDRRRRRDDDDATGGAGGTGG
GATCGAAAAGCTTTG CPA/crtB-R (Seq ID NO: 38):
GCACAGATGCGTAAGGAGAAAATACCGCATTAAACGGGGCGCTGCCAGAG
ATCAG The pUC19 was amplified by primer pair of CPA/puc19-F and (Seq ID NO:27) and CPA/puc19-R (Seq ID NO:28). Five fragments crtE, crtX, crtY, crtI and crtB were amplified by the corresponding primer pairs (Seq ID NOs: 29-38). After the PCR reaction, the resulting solution were incubated at 37° C. for 30 min with 1 µL DpnI restriction enzyme to digest DNA fragments. The PCR products were gel purified from 1% argarose gel using a Gel Purification Kit according to the manufacturer's protocol. Concentration of nucleic acids were measured using NanoDrop 2000.

Figure 6:
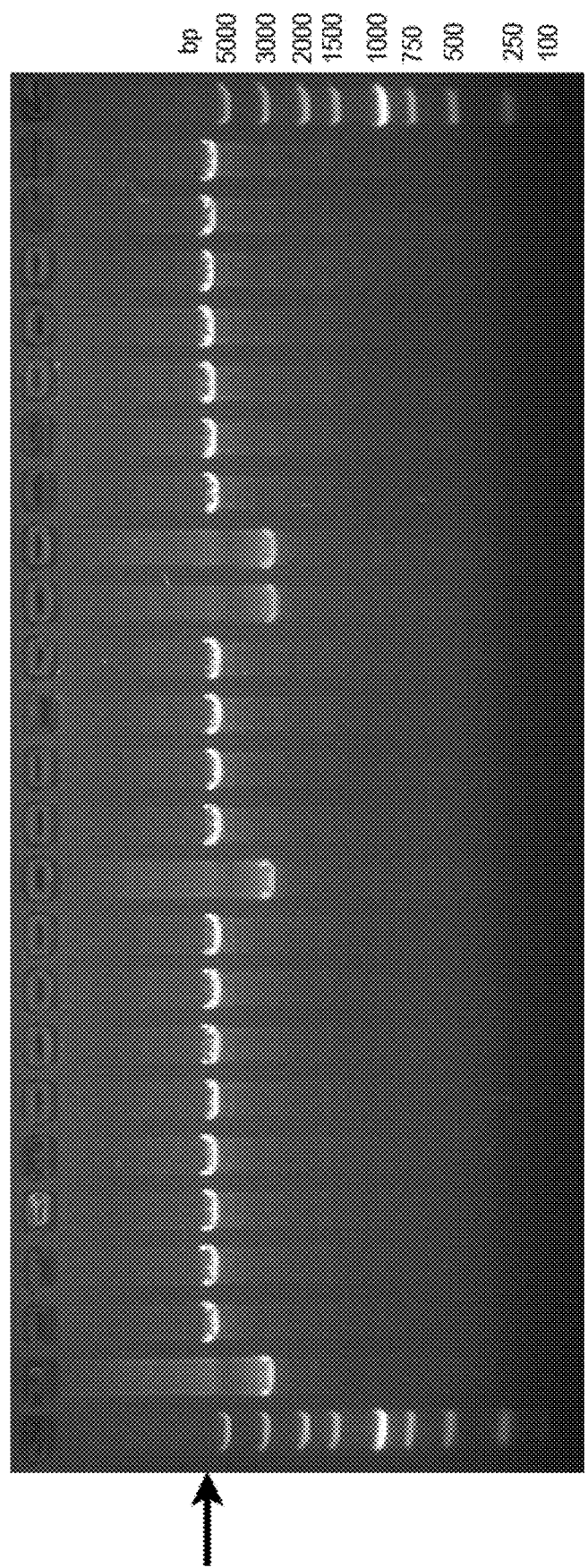
FIG. 6. Gel electrophoresis verification of assembled genes of β-carotene synthesis pathway. The arrow indicates the correct strips at 5.8 kb.

The DATEL reaction was performed in a 15 µL volume containing 1.5 µL 10×Taq DNA ligase buffer, 50 ng of five fragments (crtE, crtX, crtY, crtI and crtB), 50 ng vector pUC19, 0.2 µL Pfu super DNA polymerase, 0.2 µL Taq DNA polymerase, 1 µL Taq DNA ligase and double distilled water. The reaction was performed with the following thermal cycles: 2 min at 94° C.; 3 cycles of 30 sec at 94° C., 1 min at 50° C., 30 min at 68° C., and 5 min at 50° C.; and final 10 min at 60° C. The resulting solution were transferred into competent cell, plated in LB medium containing 100 µg/mL ampicillin and incubated at 37° C. for 30 min. The CFUs of colonies were counted. The efficiency of assembly was 800 CFU/mg DNA for 6 fragments (8.4 kb) assembly. As shown in FIG. 6, 19 of 23 recombinants showed correct size of assembly DNA in PCR verification. From further sequencing analysis, all colonies that were verified in PCR reactions were confirmed to be accurately assembled, and only 17% of total colonies had incorrect assembly due to loss of fragments during the assembly process.

Figure 7:
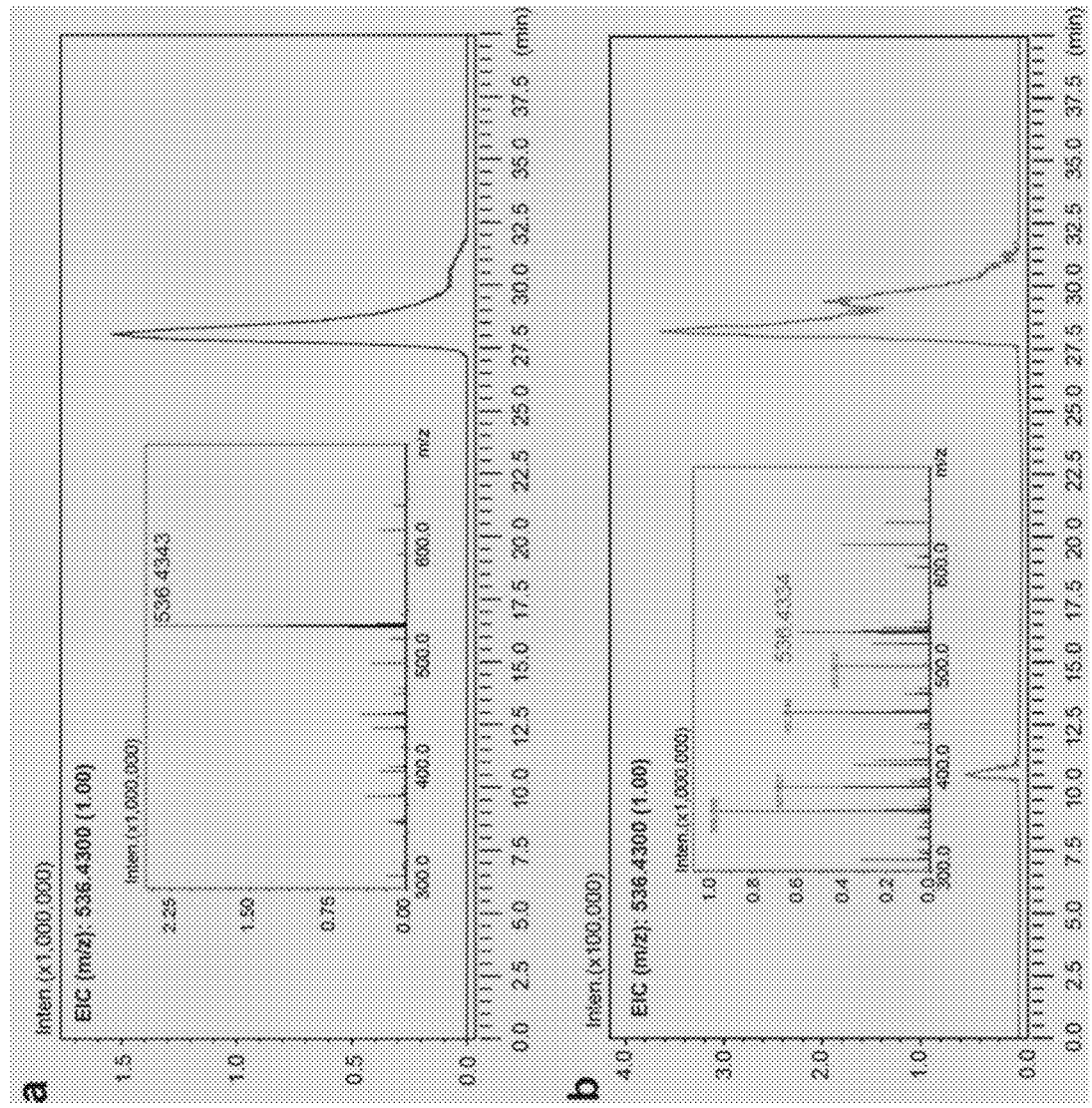
FIG. 7. Verification of β-carotene produced by recombinant strains using mass spectrometer. (a) standard β-carotene; (b) β-carotene produced by recombinant strain.
Figure 8:
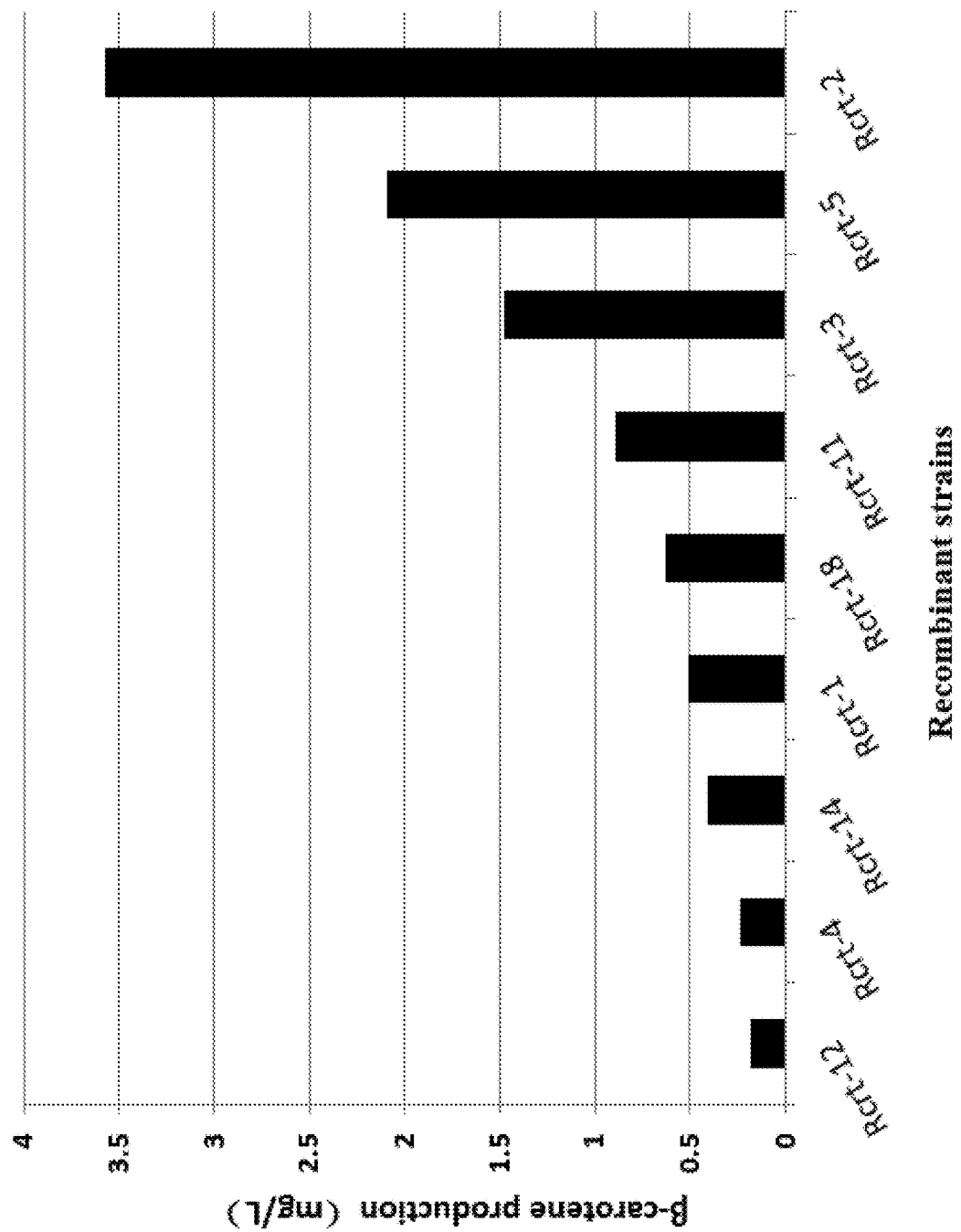
FIG. 8. Production of β-carotene from 9 recombinant strains selected from combinatorial mutation libraries of β-carotene synthesis pathway.

The colonies with obvious color difference were transferred into flasks, and cultivated to analyze the effect of DATEL in constructing mutation libraries for synthetic pathways. The colonies were inoculated in 5 mL LB medium containing 100 µg/mL ampicillin, and cultivated at 37° C. under 200 rpm for 16 hr. They were then transferred into 50 mL LB medium containing 50 g/L glucose and 100 µg/mL ampicillin, and cultivated at 37° C. under 200 rpm for 30 hr. Cells were centrifuged at 10000 rpm for 5 min and cell precipitation was collected. The cells were resuspended by equal volume acetone and incubated at 55° C. for 15 min in dark. Supernatant containing β-carotene were collected after centrifugation at 14000 rpm for 10 min. The β-carotene was qualitatively and quantitatively analyzed by LCMS-IT-TOF (Shimadzu, Japan) equipped with C18 column ((250 mm×4.6 mm, 5 µm, Waters), with a mobile phase of methanol, acetonitrile and dichloromethane in a ratio of 21:21:8(v/v/v). The flow rate was 1 mL/min. The standard β-carotene sample was bought from Sigma (Sigma-Aldrich, USA). The detection of β-carotene produced from recombinant strains were shown in FIG. 7. At about 27.5 min of retention time, peaks with charge-mass ratio of 536.43 m/z were both observed in the mass chromatogram of β-carotene in standard and sample extracted from strains' culture. The further quantitation shows (FIG. 8) that the highest yield of β-carotene from recombinant strains was 3.56 mg/L, which was 20 times more than that of the lowest yield (0.18 mg/L), indicating the successful application of DATEL technique in construction of synthetic pathway libraries.

Example 4. Assembly of Nonphosphorylated DNA Fragments

Figure 9:
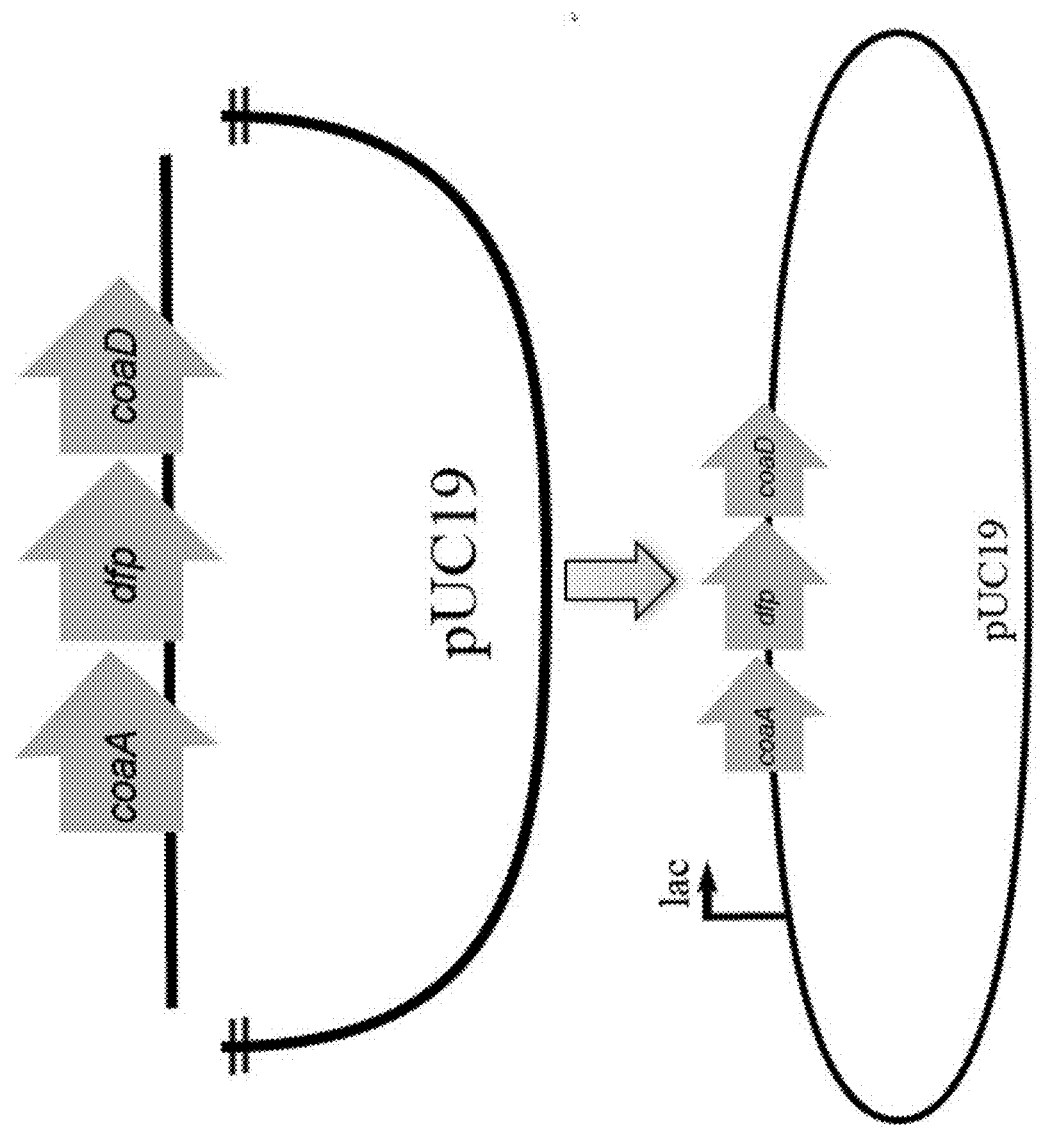
FIG. 9. Illustration of assembly of genes in coenzyme A synthesis pathway.

Genes in coenzyme A (coA) synthesis pathway from *E. coli* were used for verifying assembly capability of DATEL techniques in assembling multiple nonphosphorylated fragments. The gene cluster in coA synthesis pathway includes three DNA fragments: coaA, dfp and coaD. The above fragments were assembled into vector pUC19 as shown in FIG. 9. The primers used in this example were as follows:

COA/puc19-F (Seq ID NO: 39):
TGATGGCGAAGTTAGCGTAGGTCATAGCTGTTTCCT

COA/puc19-R (Seq ID NO: 40):
CTCTTTTATACTCATTACGAGCCGGAAGCATAAAG

COA/coaA-F (Seq ID NO: 41):
TGCTTCCGGCTCGTAATGAGTATAAAAGAGCAAACGTTAAT

COA/coaA-R (Seq ID NO: 42):
ACCGGCCAGGCTCATTTATTTGCGTAGTCTGACCTCTTCT

COA/dfp-F (Seq ID NO: 43):
AGACTACGCAAATAAATGAGCCTGGCCGGTAAAAAAATCG

COA/dfp-R (Seq ID NO: 44):
CGCCCGTTTTTGCATTTAACGTCGATTTTTTTCATCATAA

COA/coaD-F (Seq ID NO: 45):
AAAAATCGACGTTAAATGCAAAAACGGGCGATTTATCCGG

COA/coaD-R (Seq ID NO: 46):
CAGCTATGACCTACGCTAACTTCGCCATCAGCGCC

The vector pUC19 was amplified by primers COA/puc19-F (Seq ID NO:39) and COA/puc19-R (Seq ID NO:40). The fragments of coaA, dfp, and coaD were amplified by the corresponding primers (Seq ID NOs: 41-46). The resulting PCR products were incubated at 37° C. for 30 min with 1 µl DpnI to digest the DNA fragments, and then gel purified from 1% agarose gel using a Gel Purification Kit according to the manufacturer's protocol. Concentration of nucleic acids were measured using NanoDrop 2000.

Figure 10:
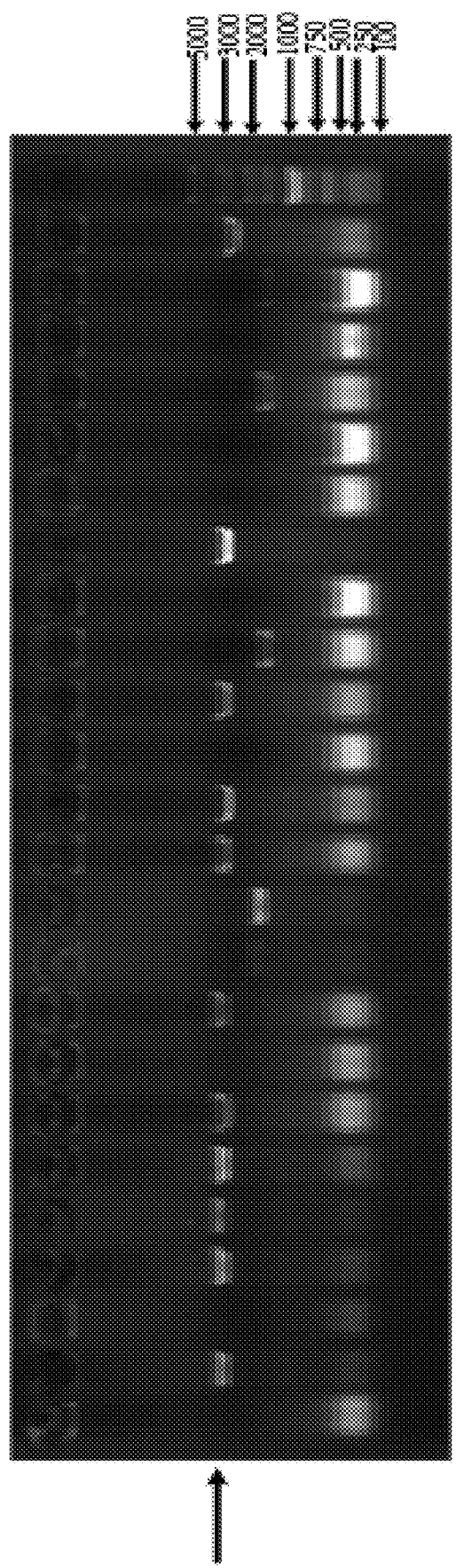
FIG. 10. Verification of the accuracy of four DNA fragments (coaA, dfp, coaD and pUC19) assembly. The arrow indicates the correct strips at 2.5 kb.

The assembly reaction was performed in a 15 µL volume containing 1.5 µL 10×MTL solution, 50 ng of three fragments (coaA, dfp, coaD), 50 ng vector pUC19, 0.2 µL Taq DNA polymerase, 1 µL Taq DNA ligase and double distilled water. The reaction was performed with the following thermal cycles: 2 min at 94° C.; 3 cycles of 30 s at 94° C., 1 min at 50° C., 10 min at 68° C., and 5 min at 50° C.; and 10 min at 60° C. The resulting solution were transferred into competent cells, plated in LB medium containing 100 µg/mL ampicillin and incubated at 37° C. for 30 min. The CFUs of colonies were counted. The efficiency of assembly was 450 CFU/µg DNA for this four-fragment (5.1 kb) assembly. As shown in FIG. 10, 55% of the total recombinants showed incorrect assembly in PCR verification, while 45% of which were assembled successfully. From further sequencing analysis, all the colonies that were verified by the PCR analysis were confirmed to be accurately assembled.

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed is:

1. A method for fast scarless in vitro DNA assembly, comprising
   a) obtaining DNA subfragments with overlapping end sequences, wherein said DNA subfragments with overlapping end sequences are generated by polymerase chain reactions (PCR) that uses primers to add said overlapping end sequences to said DNA subfragments;
   b) denaturing and annealing said DNA subfragments so that said DNA subfragments are annealed in an order according to their overlapping end sequences and unpaired single-stranded flap sequences are generated;
   c) digesting said single-stranded flap sequences using thermostable DNA polymerases with 3'-5' and/or 5'-3' single-strand specific exonuclease activity, resulting in an assembled sequence with nicked gaps;
   d) covalently sealing said nicked gaps using a thermostable ligase to form a scarless assembled sequence; and
   e) optionally repeating steps b) to d) for more than one time.

2. The method of claim 1, wherein said overlapping end sequences have 20-70 bp.

3. The method of claim 2, wherein said overlapping end sequences have 30 bp.

4. The method of claim 2, wherein said primers for amplifying said DNA subfragments contain mutated bases.

5. The method of claim 1, wherein said denaturing is performed at 98-85° C., said annealing at 35-70° C., said digesting at 45-72° C. for 5-35 min, and said sealing at 40-68° C. for 1-10 min.

6. The method of claim 2, wherein 5' termini of said primers and said DNA subfragments are phosphorylated.

7. The method of claim 1, wherein said thermostable DNA polymerases with 3'-5' single-strand specific exonuclease activity is Taq DNA polymerase and said thermostable DNA polymerases with 5'-3' single-strand specific exonuclease activity is Pfu DNA polymerase.

8. The method of claim 1, wherein said thermostable ligase is Taq DNA ligase.

9. The method of claim 1, wherein said denaturing is performed at 94° C., said annealing at 50° C., said digesting at 68° C. for 30 min, and said sealing at 50° C. for 5 min, wherein steps b) to d) are repeated for three times.

10. The method of claim 1, wherein said in vitro DNA assembly is carried out in a 15 μL reaction system containing 50 ng said DNA subfragments, 1.5 μL 10×Taq DNA ligase buffer, 0.2 μL Pfu DNA polymerase, 0.2 μL Taq DNA polymerase, and 1 μL Taq DNA ligase; wherein said reaction system is preheated at 94° C. for 2 min, undergoes three cycles of denaturing at 94° C. for 30 sec, annealing at 50° C. for 1 min, digesting at 68° C. for 30 min, and ligating at 50° C. for 5 min, and is finally heated at 66° C. for 10 min.

11. A method for fast scarless in vitro DNA assembly, comprising
   a) obtaining DNA subfragments with overlapping end sequences;
   b) denaturing and annealing said DNA subfragments so that said DNA subfragments are annealed in an order according to their overlapping end sequences and unpaired single-stranded flap sequences are generated;
   c) digesting said single-stranded flap sequences using thermostable DNA polymerases with 3'-5' and/or 5'-3' single-strand specific exonuclease activity, resulting in an assembled sequence with nicked gaps;
   d) covalently sealing said nicked gaps using a thermostable ligase to form a scarless assembled sequence; and
   e) optionally repeating steps b) to d) for more than one time.

* * * * *

SEQUENCE LISTING

<160> NUMBER OF SEQ ID NOS: 46

<210> SEQ ID NO 1
<211> LENGTH: 46
<212> TYPE: DNA
<213> ORGANISM: Artificial Sequence
<220> FEATURE:
<223> OTHER INFORMATION: PCR Primer

<400> SEQUENCE: 1
ttcttctccc ttacccatgg cgtaatcatg gtcatagctg tttcct                46

<210> SEQ ID NO 2
<211> LENGTH: 43
<212> TYPE: DNA
<213> ORGANISM: Artificial Sequence
<220> FEATURE:
<223> OTHER INFORMATION: DNA Primer

<400> SEQUENCE: 2
tggatgaact atacaaataa ctggccgtcg ttttacaacg tcg                   43

<210> SEQ ID NO 3
<211> LENGTH: 28
<212> TYPE: DNA
<213> ORGANISM: Artificial Sequence
<220> FEATURE:
<223> OTHER INFORMATION: DNA Primer

<400> SEQUENCE: 3
ccatgggtaa gggagaagaa cttttcac                                    28

<210> SEQ ID NO 4
<211> LENGTH: 24
<212> TYPE: DNA
<213> ORGANISM: Artificial Sequence
<220> FEATURE:
<223> OTHER INFORMATION: DNA Primer

<400> SEQUENCE: 4
ttatttgtat agttcatcca tgcc                                        24

<210> SEQ ID NO 5
<211> LENGTH: 30
<212> TYPE: DNA
<213> ORGANISM: Artificial Sequence
<220> FEATURE:
<223> OTHER INFORMATION: DNA Primer

<400> SEQUENCE: 5
catgattacg ccatgggtaa gggagaagaa                                  30

<210> SEQ ID NO 6
<211> LENGTH: 30
<212> TYPE: DNA
<213> ORGANISM: Artificial Sequence
<220> FEATURE:
<223> OTHER INFORMATION: DNA Primer

<400> SEQUENCE: 6
cgacggccag ttatttgtat agttcatcca                                  30

<210> SEQ ID NO 7
<211> LENGTH: 40
<212> TYPE: DNA
<213> ORGANISM: Artificial Sequence

```
<220> FEATURE:
<223> OTHER INFORMATION: DNA Primer

<400> SEQUENCE: 7
cagctatgac catgattacg ccatgggtaa gggagaagaa                           40

<210> SEQ ID NO 8
<211> LENGTH: 40
<212> TYPE: DNA
<213> ORGANISM: Artificial Sequence
<220> FEATURE:
<223> OTHER INFORMATION: DNA Primer

<400> SEQUENCE: 8
cgttgtaaaa cgacggccag ttatttgtat agttcatcca                           40

<210> SEQ ID NO 9
<211> LENGTH: 50
<212> TYPE: DNA
<213> ORGANISM: Artificial Sequence
<220> FEATURE:
<223> OTHER INFORMATION: DNA Primer

<400> SEQUENCE: 9
acacaggaaa cagctatgac catgattacg ccatgggtaa gggagaagaa                50

<210> SEQ ID NO 10
<211> LENGTH: 50
<212> TYPE: DNA
<213> ORGANISM: Artificial Sequence
<220> FEATURE:
<223> OTHER INFORMATION: DNA Primer

<400> SEQUENCE: 10
ccagtcacga cgttgtaaaa cgacggccag ttatttgtat agttcatcca                50

<210> SEQ ID NO 11
<211> LENGTH: 60
<212> TYPE: DNA
<213> ORGANISM: Artificial Sequence
<220> FEATURE:
<223> OTHER INFORMATION: DNA Primer

<400> SEQUENCE: 11
taacaatttc acacaggaaa cagctatgac catgattacg ccatgggtaa gggagaagaa     60

<210> SEQ ID NO 12
<211> LENGTH: 60
<212> TYPE: DNA
<213> ORGANISM: Artificial Sequence
<220> FEATURE:
<223> OTHER INFORMATION: DNA Primer

<400> SEQUENCE: 12
cagggttttc ccagtcacga cgttgtaaaa cgacggccag ttatttgtat agttcatcca     60

<210> SEQ ID NO 13
<211> LENGTH: 70
<212> TYPE: DNA
<213> ORGANISM: Artificial Sequence
<220> FEATURE:
<223> OTHER INFORMATION: DNA Primer

<400> SEQUENCE: 13
tgtgagcgga taacaatttc acacaggaaa cagctatgac catgattacg ccatgggtaa     60
```
gggagaagaa 70

<210> SEQ ID NO 14
<211> LENGTH: 70
<212> TYPE: DNA
<213> ORGANISM: Artificial Sequence
<220> FEATURE:
<223> OTHER INFORMATION: DNA Primer

<400> SEQUENCE: 14
tgggtaacgc cagggttttc ccagtcacga cgttgtaaaa cgacggccag ttatttgtat    60
agttcatcca                                                          70

<210> SEQ ID NO 15
<211> LENGTH: 38
<212> TYPE: DNA
<213> ORGANISM: Artificial Sequence
<220> FEATURE:
<223> OTHER INFORMATION: DNA Primer

<400> SEQUENCE: 15
ggtaatggca gtcgtgactg ggaaaaccct ggcgttac                            38

<210> SEQ ID NO 16
<211> LENGTH: 44
<212> TYPE: DNA
<213> ORGANISM: Artificial Sequence
<220> FEATURE:
<223> OTHER INFORMATION: DNA Primer

<400> SEQUENCE: 16
ctcgatgagt tcttctaacc tgtgtgaaat tgttatccgc tcac                     44

<210> SEQ ID NO 17
<211> LENGTH: 51
<212> TYPE: DNA
<213> ORGANISM: Artificial Sequence
<220> FEATURE:
<223> OTHER INFORMATION: DNA Primer

<400> SEQUENCE: 17
gttcatccgc gccaacgccg agtaacctgt gtgaaattgt tatccgctca c             51

<210> SEQ ID NO 18
<211> LENGTH: 59
<212> TYPE: DNA
<213> ORGANISM: Artificial Sequence
<220> FEATURE:
<223> OTHER INFORMATION: DNA Primer

<400> SEQUENCE: 18
attacacatg gcatggacga actatacaaa taacctgtgt gaaattgtta tccgctcac     59

<210> SEQ ID NO 19
<211> LENGTH: 44
<212> TYPE: DNA
<213> ORGANISM: Artificial Sequence
<220> FEATURE:
<223> OTHER INFORMATION: DNA Primer

<400> SEQUENCE: 19
agggttttcc cagtcacgac tgccattacc caggccgacg cagc                     44

<210> SEQ ID NO 20
<211> LENGTH: 38

<212> TYPE: DNA
<213> ORGANISM: Artificial Sequence
<220> FEATURE:
<223> OTHER INFORMATION: DNA Primer

<400> SEQUENCE: 20
cttctccctt acccataagg tggctcctac ccgtgatc                              38

<210> SEQ ID NO 21
<211> LENGTH: 40
<212> TYPE: DNA
<213> ORGANISM: Artificial Sequence
<220> FEATURE:
<223> OTHER INFORMATION: DNA Primer

<400> SEQUENCE: 21
gtaggagcca ccttatgggt aagggagaag aacttttcac                           40

<210> SEQ ID NO 22
<211> LENGTH: 27
<212> TYPE: DNA
<213> ORGANISM: Artificial Sequence
<220> FEATURE:
<223> OTHER INFORMATION: DNA Primer

<400> SEQUENCE: 22
ttatttgtat agttcgtcca tgccatg                                         27

<210> SEQ ID NO 23
<211> LENGTH: 57
<212> TYPE: DNA
<213> ORGANISM: Artificial Sequence
<220> FEATURE:
<223> OTHER INFORMATION: DNA Primer

<400> SEQUENCE: 23
attacacatg gcatggacga actatacaaa taaatgtcac aacaacagct tgaatca        57

<210> SEQ ID NO 24
<211> LENGTH: 25
<212> TYPE: DNA
<213> ORGANISM: Artificial Sequence
<220> FEATURE:
<223> OTHER INFORMATION: DNA Primer

<400> SEQUENCE: 24
ttactcggcg ttggcgcgga tgaac                                           25

<210> SEQ ID NO 25
<211> LENGTH: 51
<212> TYPE: DNA
<213> ORGANISM: Artificial Sequence
<220> FEATURE:
<223> OTHER INFORMATION: DNA Primer

<400> SEQUENCE: 25
gttcatccgc gccaacgccg agtaaatgag ccatattcaa cgggaaacgt c              51

<210> SEQ ID NO 26
<211> LENGTH: 36
<212> TYPE: DNA
<213> ORGANISM: Artificial Sequence
<220> FEATURE:
<223> OTHER INFORMATION: DNA Primer

<400> SEQUENCE: 26
caatttcaca caggttagaa gaactcatcg agcatc                                     36

<210> SEQ ID NO 27
<211> LENGTH: 29
<212> TYPE: DNA
<213> ORGANISM: Artificial Sequence
<220> FEATURE:
<223> OTHER INFORMATION: DNA Primer

<400> SEQUENCE: 27
tgcggtattt tctccttacg catctgtgc                                             29

<210> SEQ ID NO 28
<211> LENGTH: 30
<212> TYPE: DNA
<213> ORGANISM: Artificial Sequence
<220> FEATURE:
<223> OTHER INFORMATION: DNA Primer

<400> SEQUENCE: 28
ccacacaaca tacgagccgg aagcataaag                                            30

<210> SEQ ID NO 29
<211> LENGTH: 67
<212> TYPE: DNA
<213> ORGANISM: Artificial Sequence
<220> FEATURE:
<223> OTHER INFORMATION: DNA Primer

<400> SEQUENCE: 29
ctttatgctt ccggctcgta tgttgtgtgg rrrrrdddda tgatgacggt ctgtgcagaa           60
caacacg                                                                     67

<210> SEQ ID NO 30
<211> LENGTH: 27
<212> TYPE: DNA
<213> ORGANISM: Artificial Sequence
<220> FEATURE:
<223> OTHER INFORMATION: DNA Primer

<400> SEQUENCE: 30
ttaactgacg gcagcgagtt ttttctc                                               27

<210> SEQ ID NO 31
<211> LENGTH: 67
<212> TYPE: DNA
<213> ORGANISM: Artificial Sequence
<220> FEATURE:
<223> OTHER INFORMATION: DNA Primer

<400> SEQUENCE: 31
tttgagaaaa aactcgctgc cgtcagttaa rrrrrdddda tgagccactt tgcggtcatt           60
gcaccgc                                                                     67

<210> SEQ ID NO 32
<211> LENGTH: 39
<212> TYPE: DNA
<213> ORGANISM: Artificial Sequence
<220> FEATURE:
<223> OTHER INFORMATION: DNA Primer

<400> SEQUENCE: 32
ttagactgct gcgtagtctc tcctggtgag gaccggctg                                  39

<210> SEQ ID NO 33
<211> LENGTH: 64
<212> TYPE: DNA
<213> ORGANISM: Artificial Sequence
<220> FEATURE:
<223> OTHER INFORMATION: DNA Primer

<400> SEQUENCE: 33
ctcaccagga gagactacgc agcagtctaa rrrrrddddа tgccgcggta tgatctgatt    60
ctgg                                                                64

<210> SEQ ID NO 34
<211> LENGTH: 26
<212> TYPE: DNA
<213> ORGANISM: Artificial Sequence
<220> FEATURE:
<223> OTHER INFORMATION: DNA Primer

<400> SEQUENCE: 34
tcattgcatc gcctgttgac ggtgag                                        26

<210> SEQ ID NO 35
<211> LENGTH: 65
<212> TYPE: DNA
<213> ORGANISM: Artificial Sequence
<220> FEATURE:
<223> OTHER INFORMATION: DNA Primer

<400> SEQUENCE: 35
ctcctcaccg tcaacaggcg atgcaatgad drrrrrdddd atgaatagaa ctacagtaat    60
tggcg                                                               65

<210> SEQ ID NO 36
<211> LENGTH: 26
<212> TYPE: DNA
<213> ORGANISM: Artificial Sequence
<220> FEATURE:
<223> OTHER INFORMATION: DNA Primer

<400> SEQUENCE: 36
tcaagccaga tcctccagca tcaatc                                        26

<210> SEQ ID NO 37
<211> LENGTH: 65
<212> TYPE: DNA
<213> ORGANISM: Artificial Sequence
<220> FEATURE:
<223> OTHER INFORMATION: DNA Primer

<400> SEQUENCE: 37
caggattgat gctggaggat ctggcttgad drrrrrdddd atggaggtgg gatcgaaaag    60
ctttg                                                               65

<210> SEQ ID NO 38
<211> LENGTH: 55
<212> TYPE: DNA
<213> ORGANISM: Artificial Sequence
<220> FEATURE:
<223> OTHER INFORMATION: DNA Primer

<400> SEQUENCE: 38
gcacagatgc gtaaggagaa aataccgcat taaacggggc gctgccagag atcag         55

<210> SEQ ID NO 39

```
<211> LENGTH: 36
<212> TYPE: DNA
<213> ORGANISM: Artificial Sequence
<220> FEATURE:
<223> OTHER INFORMATION: DNA Primer

<400> SEQUENCE: 39
tgatggcgaa gttagcgtag gtcatagctg tttcct                            36

<210> SEQ ID NO 40
<211> LENGTH: 35
<212> TYPE: DNA
<213> ORGANISM: Artificial Sequence
<220> FEATURE:
<223> OTHER INFORMATION: DNA Primer

<400> SEQUENCE: 40
ctcttttata ctcattacga gccggaagca taaag                             35

<210> SEQ ID NO 41
<211> LENGTH: 41
<212> TYPE: DNA
<213> ORGANISM: Artificial Sequence
<220> FEATURE:
<223> OTHER INFORMATION: DNA Primer

<400> SEQUENCE: 41
tgcttccggc tcgtaatgag tataaaagag caaacgttaa t                      41

<210> SEQ ID NO 42
<211> LENGTH: 40
<212> TYPE: DNA
<213> ORGANISM: Artificial Sequence
<220> FEATURE:
<223> OTHER INFORMATION: DNA Primer

<400> SEQUENCE: 42
accggccagg ctcatttatt tgcgtagtct gacctcttct                        40

<210> SEQ ID NO 43
<211> LENGTH: 40
<212> TYPE: DNA
<213> ORGANISM: Artificial Sequence
<220> FEATURE:
<223> OTHER INFORMATION: DNA Pirmer

<400> SEQUENCE: 43
agactacgca aataaatgag cctggccggt aaaaaaatcg                        40

<210> SEQ ID NO 44
<211> LENGTH: 40
<212> TYPE: DNA
<213> ORGANISM: Artificial Sequence
<220> FEATURE:
<223> OTHER INFORMATION: DNA Primer

<400> SEQUENCE: 44
cgcccgtttt tgcatttaac gtcgattttt ttcatcataa                        40

<210> SEQ ID NO 45
<211> LENGTH: 40
<212> TYPE: DNA
<213> ORGANISM: Artificial Sequence
<220> FEATURE:
<223> OTHER INFORMATION: DNA Primer

<400> SEQUENCE: 45
```

```
aaaaatcgac gttaaatgca aaaacgggcg atttatccgg                    40
```

<210> SEQ ID NO 46
<211> LENGTH: 35
<212> TYPE: DNA
<213> ORGANISM: Artificial Sequence
<220> FEATURE:
<223> OTHER INFORMATION: DNA Primer

<400> SEQUENCE: 46

```
cagctatgac ctacgctaac ttcgccatca gcgcc                         35
```